United States Patent
Mattei (10) Patent No.: US 11,555,186 B2
(45) Date of Patent: Jan. 17, 2023

(54) WATER-SOLUBLE PROLAMIN, PREPARATION THEREOF, AND USES THEREOF FOR FOOD-GRADE APPLICATION INCLUDING PROLAMIN COMPOSITIONS COMBINING PROLAMIN AND DNA TAGGANTS

(71) Applicant: SafeTraces, Inc., Pleasanton, CA (US)

(72) Inventor: Peter Mattei, Lemon Grove, CA (US)

(73) Assignee: Safetraces, Inc., Pleasanton, CA (US)

( * ) Notice: Subject to any disclaimer, the term of this patent is extended or adjusted under 35 U.S.C. 154(b) by 155 days.

(21) Appl. No.: 16/949,085

(22) Filed: Oct. 13, 2020

(65) Prior Publication Data

US 2021/0108192 A1    Apr. 15, 2021

Related U.S. Application Data

(60) Provisional application No. 62/914,121, filed on Oct. 11, 2019.

(51) Int. Cl.
| | | |
|---|---|---|
| *C12Q 1/6806* | (2018.01) |
| *C12N 15/10* | (2006.01) |
| *C07K 14/425* | (2006.01) |
| *A23L 33/185* | (2016.01) |

(52) U.S. Cl.
CPC ........ *C12N 15/1065* (2013.01); *C07K 14/425* (2013.01); *C12Q 1/6806* (2013.01); *A23L 33/185* (2016.08); *A23V 2002/00* (2013.01)

(58) Field of Classification Search
CPC . C12N 15/1065; C07K 14/425; C12Q 1/6806
See application file for complete search history.

(56) References Cited

U.S. PATENT DOCUMENTS

| | | |
|---|---|---|
| 6,635,206 B1 | 10/2003 | Padua et al. |
| 6,849,113 B2 | 2/2005 | Padua et al. |
| 9,504,274 B2 | 11/2016 | George et al. |
| 2004/0056388 A1 | 3/2004 | Padua et al. |
| 2011/0189353 A1 | 8/2011 | George et al. |
| 2015/0004102 A1* | 1/2015 | Salman .................. A61Q 19/00 424/452 |
| 2015/0322426 A1* | 11/2015 | Zografos ............ C12N 15/1065 426/531 |
| 2017/0027208 A1 | 2/2017 | Given |

FOREIGN PATENT DOCUMENTS

CN    110106577    *  9/2019

* cited by examiner

*Primary Examiner* — Kenneth R Horlick
(74) *Attorney, Agent, or Firm* — Haynes and Boone LLP (57) ABSTRACT

A water-soluble prolamin composition, such as a zein composition, and methods for producing the same. A method for tagging items comprising applying a plurality of non-coding DNA tags in a prolamin composition, such as a zein composition, wherein the selection of the particular taggants corresponds with a binary or nonbinary code sequence containing information about the tagged items.

20 Claims, 5 Drawing Sheets

WATER-SOLUBLE PROLAMIN, PREPARATION THEREOF, AND USES THEREOF FOR FOOD-GRADE APPLICATION INCLUDING PROLAMIN COMPOSITIONS COMBINING PROLAMIN AND DNA TAGGANTS

CROSS-REFERENCES TO PRIORITY AND RELATED PATENTS/APPLICATIONS

This application claims the benefit of, and priority from, U.S. Provisional Patent Application No. 62/914,121 filed Oct. 11, 2019, entitled "Water Soluble Prolamine"

This application may reference the following:

International Patent Application No. PCT/US2015/028880 filed May 1, 2015, entitled "DNA Based Bar Code for Improved Food Traceability", and naming Zografos, et al. (hereinafter "Zografos I");

International Patent Application No. PCT/US2016/038083 filed Jun. 17, 2016, entitled "Pathogen Surrogates Based on Encapsulated Tagged DNA For Verification of Sanitation and Wash Water Systems for Fresh Produce", and naming Zografos, et al. (hereinafter "Zografos II");

International Patent Application No. PCT/US2019/013069 filed Jan. 10, 2019, entitled "Dispensing System for Applying DNA Taggants Used in Combinations to Tag Articles", and naming Zografos, et al. (hereinafter "Zografos III");

International Patent Application No. PCT/US2019/017123 filed Feb. 7, 2019, entitled "Source and Sanitation Assurance Testing of Foodstuffs and Sensitive Applications", and naming Zografos (hereinafter "Zografos IV");

International Patent Application No. PCT/US2019/029002 filed Apr. 24, 2019, entitled "Sanitation Monitoring System Using Pathogen Surrogates and Surrogate Tracking", and naming Zografos, et al. (hereinafter "Zografos V"); and U.S. patent application Ser. No. 16/554,294 filed Aug. 28, 2019, entitled "Product Tracking and Rating System Using DNA Tags", and naming Zografos, et al. (hereinafter "Zografos VI").

The entire disclosure(s) of the patent(s)/application(s) recited above is/are hereby incorporated by reference, as if set forth in full in this document, for all purposes.

FIELD

The present disclosure generally relates to formulations of prolamins that are water-soluble. More particularly, the present disclosure describes making and using water-soluble prolamins in connection with applying DNA taggants to products in a supply chain and other items.

BACKGROUND

Prolamins are plant proteins having a high proline amino acid content. Applications that require even dispersion of prolamin, such as where it is combined with sequences of non-coding DNA in the form of combinations of DNA taggants applied to food products in a supply chain, often require that the prolamin not aggregate into clumps. One approach is to dissolve the prolamin-based taggants in solution and apply the solution to the food products, allowing the solvent to evaporate and leave well-distributed food-safe taggants on the food products.

Prolamins are typically insoluble in water but are soluble in water-ethanol mixtures and so applications that require a prolamin in solution often involve the use of ethanol although ethanol might be disfavored as a solvent in many environments. But one issue with using ethanol in an industrial process is its flammability.

There is a need for a method to produce stable, discrete zein particles, which are capable of aqueous dispersion.

SUMMARY

In some embodiments, a composition comprising prolamin and [1,3]-propanediol may be provided. In some embodiments, the prolamin comprises zein, but in other embodiments might comprise other prolamin In some embodiments, the zein comprises zein nanoparticles. The composition may be essentially free of ethanol. The composition may comprise a surfactant such as surfactin. The composition may be an aqueous solution.

In some embodiments, the composition further comprises cyclodextrin, casein, or a combination thereof. The composition may further comprise one or more stabilizers. The composition may be a powder. The powder may be prepared by drying an aqueous solution comprising prolamin, [1,3]-propanediol, cyclodextrin, and casein. The composition may further comprise a DNA taggant. The DNA taggant may comprise a unique combination of a plurality of DNA sequences.

There may be provided a method for preparing such a composition. The method may comprise obtaining a first solution comprising prolamin and [1,3]-propanediol, obtaining a second solution comprising water, and mixing the first solution with a second solution comprising water to prepare the composition. The method may further comprise mixing prolamin with [1,3]-propanediol at a first elevated temperature to form the first solution. The method may further comprise mixing prolamin with a surfactant in [1,3]-propanediol at a first elevated temperature to form the first solution. For example, the first elevated temperature can be a temperature between 90 and 115° C.

The method may further comprise adding a surfactant to zein and [1,3]-propanediol to obtain the first solution. The method may further comprise adding DNA to the first solution before adding the first solution to the second solution. For example, the DNA can be a DNA taggant, such as a unique combination of a plurality of DNA sequences. The second solution might further comprise cyclodextrin, casein, or a combination thereof. The method may further comprise freezing drying the composition to obtain a powder.

A food product comprising a composition described herein can be provided. There may be provided a pharmaceutical composition comprising the composition described herein in a pharmaceutically acceptable carrier. There may be provided a personal care composition comprising the composition.

There may be provided a method of using the composition as described herein, wherein the method comprises applying the composition to a surface of an object. The method may comprise drying the composition after applying the composition to the surface.

The method may comprise treating a wound of a subject with the composition.

A method of preparing a zein composition may be provided. The method may comprise obtaining a first solution comprising zein and [1,3]-propanediol; and b) combing the first solution with a second solution comprising water to prepare the zein composition.

Some embodiments provide aqueous solutions including zein, cyclodextrin, surfactant, and casein, in an aqueous carrier solution. In some embodiments, the solution further comprises [1,3]-propanediol. In some embodiments, the surfactant comprises surfactin. In some embodiments, the solution further comprises one or more stabilizers.

In some embodiments, the zein is nanoscale. In some embodiments, the zein can have a discrete particle size, or a discrete range of particle sizes. For example, zein or any compositions that contain zein may have at least, about or at most or below 1, 2, 3, 4, 5, 10, 15, 20, 30, 40, 50, 60, 70, 80, 90, 100, 200, 300, 400, 500, 600, 700, 800, 900, 1000 nm or any intermediate ranges or values derived therefrom in at least one dimension. In some embodiments, the zein complex has hydrophilic properties.

In some embodiments, the zein complex can be a slurry, a powder, or a liquid.

In some embodiments, there may be provided methods of producing aqueous solutions including zein, cyclodextrin, surfactant, and casein, in an aqueous carrier solution, wherein the method includes: a) reacting zein with surfactant in [1,3]-propanediol at elevated temperature, to form a Phase 1 solution, b) preparing a solution of water, cyclodextrin, and casein, to form a Phase 2 solution, and c) adding the Phase 1 solution, comprising zein, [1,3]-propanediol, and surfactant, to the Phase 2 solution, comprising water, cyclodextrin, and casein, at elevated temperature. In some embodiments, one or more liquid DNA sequences can be added to the Phase 1 solution before combining with the Phase 2 solution. In some embodiments, the DNA sequences can be used for product tagging and tracking purposes.

The following detailed description together with the accompanying drawings will provide a better understanding of the nature and advantages of various embodiments.

BRIEF DESCRIPTION OF THE DRAWINGS

Various embodiments in accordance with the present disclosure will be described with reference to the drawings, in which:

FIG. 1 (comprising FIGS. 1A-1C) illustrates an exemplary process for preparing an alcohol/zein concentrate.

FIG. 2 (comprising FIGS. 2A-2C) illustrates an exemplary process for preparing a [1,3]-propanediol/zein concentrate.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details.

Furthermore, well-known features may be omitted or simplified in order not to obscure the embodiment being described.

Modern commerce requires maximizing supply chain efficiencies, accountability, and security. The ability to track, and trace a product, and/or the components of a product, along its supply chain as well as throughout production and distribution, is becoming increasingly important and can help to address supply chain issues promptly.

This is relevant to a range of industries but is particularly important for the global food industry, which is becoming increasingly complex and widespread with respect to the origins and various locations a product and/or the components of a product pass through en route to an end user. This can include the growers associated with one or more components of a food product, any associated processing and/or packing locations, any associated modes transportation, and any distribution outlets. Contamination and/or tampering can occur at any one or more of these points, or nodes, of the lifecycle of the product.

The ability to track, and trace a product, and/or the components of a product, allows possible problems with respect to the integrity of a product, e.g., contamination, to be identified and can allow for the identification of the origin of the problem. Such technology can help minimize the occurrence of material fraud, contamination, related illnesses, and their associated costs, including recall costs, legal expenses, and associated business losses.

Currently, product tracing technologies involve numerous stations along the supply chain, from producer to packer, distributor, retailer and ultimately the consumer. Product identification is generally applied to the packaging, rather than to the product itself. However, product packaging is frequently discarded and additionally does not provide sufficient information to identify the exact source of a problem that has been introduced at some point along the production, supply, or distribution chain. In most instances when a consumer detects product contamination and/or symptoms of illness, it may be days or weeks after the purchase date. It is therefore desirable to provide an improved system and method for tracing products throughout the supply chain. Further, labeling a product with a tag that identifies two or more of the attributes of one or more of the nodes in the lifecycle of the product allows for easier, more efficient, and more accurate tracing of any possible sources of product contamination and tampering.

There is an industry need for tracking and tracing via biologically benign or inert surrogates. In the food and beverage industry in particular, such media will necessarily require food-safe materials.

In some embodiments, DNA tags can be used to trace food along multiple steps in the supply chain and ultimately to the consumer, by applying the product identification directly onto food products, at low cost, in a medium containing food-based FDA-approved sugars and a unique non-biological DNA tag. The resulting microparticle can be sprayed directly onto the product or mixed with a coating and will adhere to produce and other food surfaces. A practically limitless number of tags are possible by using synthetic or naturally occurring DNA.

A taggant set applied to a product might comprise a combination of pre-determined taggants, each formed of a non-coding DNA sequence that can be later detected by PCR or other method. A taggant might be associated with a value, such as where the presence of one taggant indicates a "1" in one binary position, the absence of that one taggant indicates a "0" in that binary position, and the set of presences and absences of taggants associated with various binary positions forms a binary word that provides information about the item in, or on, where the taggants are found. The non-coding DNA sequences might be taken from seaweed DNA or other DNA that contains sequences uncommon in other foods or marked objects. The sequences are small enough that they would not be coding sequences. A taggant that is applied to the food or object might comprise a plurality of the non-coding DNA sequences provided as a complex with zein, mixed with cyclodextrin, surfactin, and casein. In some embodiments, the DNA can be held and/or maintained and/or encapsulated and/or retained in an amorphous matrix of zein. In some embodiments, the zein+DNA complex can be externally present, e.g., as a coating (such as, for example, a so-called "kiss coat") onto a carrier particle. In some embodiments, the coating can be formed by the interaction of cyclodextrin with casein and with surfactin. This complex can be delivered to a product in powder form, mixed with water, alcohol, wax, or some other base, and/or encapsulated. Applying the taggant to the food or object labels the food or object, in a food safe way, where the label can be in the form of a binary word having some word length with each bit of the binary word having a bit position in the binary word. According to perhaps a predetermined convention, particular non-coding DNA sequences correspond to particular bit positions, and the presence or absence of one of those non-coding DNA sequences indicates a bit value in a particular bit position of the label applied to the food or object. The presence of the tags can later be detected using DNA PCR or other techniques. With those techniques, very little of the taggant is needed for the tag label to be recognizable.

In other variations, the label comprises other than binary bits at each bit position. In some variations, the non-coding DNA sequences include a static portion that is a sequence of nucleotides that is common to all of the non-coding DNA sequences and a variable portion that distinguishes each non-coding DNA sequence from the other non-coding DNA sequences.

In some uses, the taggant in effect labels a food or item at the source of production and in the case of food, the taggant can be detected at the point of consumption, even if all packaging is removed. In some uses, the taggant serves as a signal for sanitation practices, such as where the taggant is applied to a surface that is to be sanitized and presence of any, or more than a threshold amount of, taggant is an indication of inadequate sanitation.

The label applied by the taggant can represent a producer identity, a product identifier, a time/date of production, or other data determinable when the taggant is applied.

In one method, items are tagged by having applied thereon a plurality of non-coding DNA tags, wherein a selection of particular tags corresponds with a binary or nonbinary code sequence containing information about tagged items and wherein a non-coding DNA tag comprises a DNA sequence that would not otherwise be present in a tagged item. The DNA tags are non-coding in that they are not coding sequences of DNA that might be part of a cellular operation of coding for protein production and other uses of coding DNA. The items tagged might be food items. The information might include information as to a source of those food items. In another variation, the items tagged are surfaces requiring sanitary handling and the information includes information as to whether the surfaces were sanitized sufficiently.

The DNA tags can be selected from among a set of DNA tags that represents and/or corresponds to a label that is a binary word with bits in bit positions corresponding to whether a particular DNA tag was selected, and wherein the DNA tags of the selection are combined with a carrier to form a taggant that is applied to surfaces requiring sanitary handling or items to be tagged. For example, within a particular vendor or operator's system, if information is representable by an N-bit value, an item can be tagged by DNA tags selected from a set of N DNA tags by applying those DNA tags of the set that correspond to one bit value of the N-bit value (e.g., where a "1" is present in a bit position i in the N-bit value, the i-th DNA tag of the set of DNA tags is included in the material applied to the tagged item and where a "0" is present in a bit position i in the N-bit value, the i-th DNA tag of the set of DNA tags is not included in the material applied to the tagged item, or other variation). In some embodiments, instead of the i-th bit being represented by the presence or absence of the i-th DNA tag of the set of DNA tags, there are 2N DNA tags in the set of DNA tags, with one DNA tag (the i-th "0" tag) being applied to the tagged item if "0" is in bit position i in the N-bit value and another DNA tag (the i-th "1" tag) being applied to the tagged item if "1" is in bit position i in the N-bit value. Other than binary encoding is possible.

The DNA tags are applied as a complex with a carrier composition comprising zein, mixed with cyclodextrin, surfactin, and casein. For example, the carrier composition can be prepared as a liquid zein-in-[1,3]-propanediol (e.g., Zemea® propanediol) concentrate. The carrier composition can be further prepared from combining Phase 1 (a solution of zein solubilized with surfactant (e.g., surfactin) and [1,3]-propanediol) with Phase 2 (an aqueous formulation of water, cyclodextrin and casein). At this point, a stable water-soluble solution of self-assembled carriers can be directed through the appropriate dosing equipment with minimal or no accumulation within production devices. Delivery can optionally involve a further carrier, such as air, water, alcohol or other volatile substance, a wax, a powdering agent, and/or microbeads.

In some variations, information relating to the tagging and/or labeling process are recorded, in a public blockchain and might include one or more of a time of production, a name of a company, production details, a type of food, a supervisor name, a batch size, an expected customer, a serial number of a taggant dispenser, a label assigned to a batch, a code alphabet, error correction used, a taggant suspension type, and/or sequences of DNA nucleotides used for the plurality of non-coding DNA tags.

A method is described for tagging items comprising applying a plurality of non-coding DNA tags, wherein a selection of particular tags corresponds with a binary or nonbinary code sequence containing information about the items.

An apparatus is described for tagging items comprising applying a plurality of non-coding DNA tags, wherein a selection of particular tags corresponds with a binary or nonbinary code sequence containing information about the items.

A reading apparatus might be used for reading tags from tagged items tagged with a plurality of non-coding DNA tags, wherein a selection of particular tags corresponds with a binary or nonbinary code sequence containing information about the tagged items.

Further detail regarding DNA tagging technology in some embodiments is provided in Zografos I, Zografos II, Zografos III, Zografos IV, Zografos V, and/or Zografos VI.

The present disclosure encompasses techniques described and suggested herein which include forming binary (or non-binary) sequences that are encoded by the presence and/or absence of tags each comprising non-coding DNA snippets.

To better simulate a range of pathogenic substances (such as prions, viroids, viruses, and the like), a need exists for particles in the low-nanometer range, which can range in size from below 10 nanometers and greater. There is a need for the ability to achieve surface attachment of nano-tags with little change in aerosol or liquid dispersion characteristics.

Current tagging technology relies upon coating or attaching tags carried by molecular carriers onto commercial products. Various platforms can be used to deliver these molecular carriers. These include, for example, gelatins, proteins, saccharides, dextrins, poly-lactides, etc., and the like. However, such materials tend to exhibit aggregation either while in storage or upon dispersion. Such aggregation greatly reduces the surface area coverage by the molecular carriers. This leads to inefficient tagging and increased costs.

An exemplary carrier for DNA markers is the protein zein, which is a prolamin found in corn or maize, as zein is capable of efficiently binding with DNA. However, zein is difficult to control or design with regard to its particle segregation in aqueous media, which is ubiquitous, such that zein, by itself, is not a candidate for aqueous dispersion. It immediately aggregates, forming a tenacious gum which is incompatible with production processes. In addition, it is difficult to control and design the zein particle size distribution.

The need therefore exists for a method to result in stable, discrete zein particles, which are capable of aqueous dispersion. Such stable, discrete zein particles should exhibit a maximum surface area for a given mass; this can be used for efficiently and stably binding (i.e. transporting) DNA marker sequences. This can be achieved via a combination of small particle size and particle segregation within a multi-lamellar architecture.

In various examples and details provided herein, zein is used as an example. Unless otherwise indicated, other prolamins could be used instead of zein. Where a different prolamin is used, different proportions and/or components might be used that are in variance with those described herein for use with zein. Such variances and differences might be derived and determined based on differences between zein and that different prolamin Smaller particles produce a greater surface area per given unit mass. Using greater surface area translates into an increased efficiency of dispersion for the DNA taggants carried by the particles. As such, closely controlled particle sizing is mandatory for cost-effective dose planning.

This technology relies upon the discrete molecular forms displayed in, for example, colloids, Pickering emulsions, liposomes and nanosomes, etc., and the like, ranging in particle size from tens of microns down to 100 nanometers, and below.

Forming nanometric-scale particles with zein has heretofore proven difficult due to its amorphous organic architecture, as a combination of water and alcohol is required to achieve adequate solubility for zein. Additionally, traditional methods of batch production or spray-drying cannot accommodate an alcohol fraction due to the human safety and explosion hazards.

An alternative method is high-alkaline solution quenching; however, this technique is not appropriate for use of zein as a DNA carrier due to the high pH requirements, which rapidly degrade DNA taggants.

As disclosed herein, co-reacting zein with cyclodextrin, casein, and surfactant (e.g., surfactin) imparts nano-scale zein with hydrophilic properties, while achieving a desired particle size.

In some embodiments, zein is first reacted with [1,3]-propanediol as a solvent (e.g., Zemea® [1,3]-propanediol made by Dupont Tate & Lyle). This reaction solubilizes zein with a surfactant (e.g., surfactin) and [1,3]-propanediol at a temperature above the zein's melt/dissolution-point. Upon cooling to room temperature, a stable Phase 1 is achieved.

Phase 2 includes an aqueous formulation of water, cyclodextrin and casein.

Phase 1 is then combined with Phase 2.

Surfactin is a non-limiting exemplary surfactant which can be used in certain embodiments. Surfactin is highly efficient, food safe, and new-to-market, and has heretofore never been utilized in this area. Casein exhibits a uniquely entangled architecture, with abundant sites for intercalating the DNA-doped zein particles, onto which cyclodextrin can be "capped" or grafted.

In some embodiments, [1,3]-propanediol, zein, and surfactant are used in the following ratios:
1. Liquid Concentrate as stand-alone formulation—Phase 1: 87.5%-90% Zemea propanediol+10% zein+1.0%-2.5% Surfactin;
2. Powder Taggant—Phase 2: [7.7% liquid taggant (Phase 1)]+[61.54% Cyclodextrin]+[30.76% Casein].

In some embodiments, the product is prepared as a spray-dried powder product. It is prepared in deionized or distilled water with enough water molecules to allow complete self-assembly of the particles. The relative percentages listed herein relate to the percent active of each component and does not include water mass.

In some embodiments, Phase 1 can be prepared by bringing both the [1,3]-propanediol and zein to an elevated temperature, such as at least, about or at most 90, 95, 100, 110, 115° C. or any values or ranges derived therefrom. Surfactin can then be added with stirring, and the temperature can be elevated to or maintained at an elevated temperature of at least, about or at most 90, 95, 100, 110, 115, 120, 130, 135° C. or any values or ranges derived therefrom for a dwell time of at least, about or at most 5, 10, 20, 30, 40, 50 minutes or any ranges or values derived therefrom, covered, with continuous stirring.

The Phase 1 solution can be monitored to determine the optical clarity point of the system. Once the solution becomes optically clear, the heat can be removed, and the cooling can be started prior to the optional addition of DNA taggants. Upon cooling below 10, 20, 30, 40, 50, 60° C. or any values or ranges derived therefrom, Phase 1 can optionally be doped with a particular liquid DNA sequence(s). While still under moderate stirring, the DNA-doped concentrate solution is allowed to continue cooling to ambient temperature, such as a temperature of between 18 and 24° C. (64-75° F.) or any ranges or values derived therefrom.

In some embodiments, Phase 2 can be prepared at ambient temperature by placing water under stirring conditions and slowly adding cyclodextrin, to yield an optically clear solution. Casein is then added until fully solubilized. This mixture is aggressively stirred using, for example, a 500, 100, 2000, 2500, 3000, 4000, 5000 RPM (or any ranges or values derived therefrom) rotation (e.g., open impeller) for at least, about or at most 5, 10, 20, 30, 40, 50 minutes or any ranges or values derived therefrom. In some embodiments, this mixture can be assembled using an in-line homogenizer, an overhead homogenizer, or high-pressure microfluidizer.

In some embodiments, both Phase 1 and Phase 2 are then heated to around 50° C. and combined using slow delivery of Phase 1 into Phase 2. Slow delivery might be achieved via metered dosing equipment, small-diameter peristaltic pump, needle injection or using a device capable of inserting continuous small quantities of the Phase 1 liquid concentrate over a period of time. Such time should be 20 minutes or more, in certain embodiments, to allow the self-assembly reaction of the two phases.

In some embodiments, the zein complex can be prepared by bringing the Phase 1 concentrate up to a temperature of at least, about or at most 90, 95, 100, 110, 115, 120, 130, 135° C. or any intermediate values or ranges derived therefrom, on a stirring hotplate with 10, 50, 100, 200, 300, 400, 500, 100 RPM rotation or any intermediate values or ranges derived therefrom.

Second, the aqueous Phase 2 can be brought at least, about or at most 30, 40, 50, 60, 70, 80, 90, 100° C. or any intermediate values or ranges derived therefrom and stabilized there, at a stir setting at 10, 50, 100, 150, 200, 250, 300, 350, 400, 450, 500, 100 RPM rotation or any intermediate values or ranges derived therefrom with a magnetic bar or stir paddle which does not form a vortex funnel to the bottom of the container. Ideally, stir speed should just form a surface vortex which extends no lower than 30% below the surface.

Next, a metering dosing pump is used to slowly add the Phase 1 concentrate into the aqueous Phase 2 under continuous slow stirring. Once the formulation is complete, the heat is turned-off, and the vessel is allowed to return to room temperature with slow stirring. The aqueous zein complex can then be stored for use later.

In some embodiments, the aqueous zein complex can be described as a slurry.

In some embodiments, stabilizers can be added, such as, for example, microcrystalline cellulose(s).

In some embodiments, zein may be mixed with a surfactant in [1,3]-propanediol at a first elevated temperature to form a Phase 1 concentrate. The first elevated temperature may be any temperature above room temperature but not to exceed 115° C. In some embodiments, the first elevated temperature may be any temperature above zein's melt/dissolution point, for example, between 90 to 115° C. or any values or ranges derived therefrom. For example, the propanediol of phase 1 may be brought to 90° C. and slowly brought to 115° C. under moderate, 350 rpm stir. After full dissolution of the zein as an optically clear liquid in [1,3]-propanediol, a surfactant such as surfactin is added and allowed to fully disperse, eventually transitioning to an optically clear liquid. The mixture can be allowed to dwell for 10 minutes at 115° C. or for 20 minutes at 135° C. The temperature is then brought down to below 80° C., more preferably 70° C. in order to add the DNA without degradation.

Under shear, zein agglomerates, a suitable blade type, shape and speed can be selected to minimize zein agglomeration. A broad, flat blade design or a magnetic stir bar may be used to create enough turbulence to move the ingredients throughout the liquid mass without forming a deep vortex. For example, a stir at 250 to 350 RPM or any intermediate ranges or values derived therefrom may be used to form a Phase 1 solution while achieving a desired turbulence.

In some embodiments, water, cyclodextrin, and casein may be prepared in a solution to form a Phase 2 solution. Phase 2 solution may be brought to between 70 and 75° C. or any intermediate values or ranges. The Phase 1 concentrate may then be poured into a vessel having a Phase 2 solution.

In some embodiments, the Phase 1 solution, comprising zein, [1,3]-propanediol, and surfactant at a second elevated temperature may be added to the Phase 2 solution, comprising water, cyclodextrin, and casein, the Phase 2 solution at a second elevated temperature. The second elevated temperature of Phase 1 may be lower than or at or up to around 5° C. below the third elevated temperature of Phase 2. For example, Phase 2 at 72° C. might be mixed with Phase 1 at 67 to 72° C. Mixing speed during the combining of the two phases is such that a minimal but perceptible vortex forms at the surface of the combined solution.

One skilled in the art will appreciate that the above-described experimental procedures are exemplary. One skilled in the art will further understand where modification of the above-described process can achieve comparable results, i.e. formation of an aqueous zein complex. One skilled in the art will further be able to determine varying concentrations of the components used in formation of the aqueous zein complex. Zein As is known to those skilled in the art, zein is not soluble in 100% water or 100% alcohol. However, zein exhibits good solubility in systems that comprise greater than 60% alcohol or systems that utilize ammonia or highly alkaline aqueous carriers. Unfortunately, such constraints pose problems with manufacturing, application, and safety. Alkaline aqueous carriers and/or ammonia are not food safe, and therefore prohibit using zein in many food and pharma applications.

In some embodiments, the presently described zein complexes eliminate alcohol, thereby removing a solvent that can pose problems during both initial formulation as well as downstream application. The chemistries utilized to form the zein complexes described herein allow for the manufacturing of a stable, food safe zein concentrate without alcohol, ammonia, or pH modifiers. This concentrate shows good shelf stability and can go into water, whereupon it self-assembles into nanosomal structures.

Currently, a composition may be provided that contains 10% zein in a food-safe carrier solution. In some embodiments, the composition may encompass concentrates ranging from less than about 0.5% to about 15%, and greater, zein in a food-safe carrier solution. For example, the composition may encompass concentrates of about 0.5%, 1.0%, 1.5%, 2.0%, 2.5%, 3.0%, 3.5%, 4.0%, 4.5%, 4.7%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, and greater or any intermediate values or ranges derived therefrom, zein in a food-safe carrier. The composition may be a solution or a solid, e.g., a dried powder.

Surfactant

Surfactin (Kaneka) can be used as the surfactant for the complex in some embodiments, as the use of a (lipo) polypeptide surfactant represents a highly efficient method of non-aggregation. Surfactin is a cyclic lipopeptide-based biosurfactant produced by a harmless microbe, namely *Bacillus subtilis*. Surfactin is a new-to-market surfactant, which is far more efficient than synthetic or natural surfactants. For example, surfactin has a hydrophilic-lipophilic balance (HLB) of 10-12, indicating it can freely dissolve in a mixture of water and oil phases, whereas phosphatidyl-choline (as soy lecithin) has an HLB of 8; this latter value is at the low range of efficiency in creating oil-in-water dispersions. As such, small amounts of surfactin can achieve and maintain non-aggregation of zein, and/or a liquid taggant, such as a DNA taggant.

Polymeric micelles are made of the surfactin amphiphilic copolymer with a core-shell structure. At levels above its critical micelle concentration, the amphiphilic polymer (surfactin) self-assembles into a micellar structure, with the outer shell being hydrophilic and inner core (prolamin) being hydrophobic. The hydrophobic core can encapsulate poorly water-soluble actives, while the hydrophilic shell can help to solubilize the micelles.

In some embodiments, zein is loaded with a surfactant such as surfactin at a zein : surfactant ratio of about, at least, or at most 5:1, 10:1, 20:1, 30:1, 40:1, 50:1, 60:1, 70:1, 80:1, 90:1, 100:1, 1000:1 or any intermediate ranges or values derived therefrom (e.g., the ratio is a weight ratio). In some embodiments, a loading of a surfactant such as surfactin of about, at least, or at most 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or any intermediate ranges or values derived therefrom (e.g., % refers to weight percentages) can be used to be mixed with zein and [1,3]-propanediol.

Support Architecture

Cyclodextrin can be used as a support architecture for the complex in some embodiments. In particular, cyclodextrin creates a consistent particle. In this process, cyclodextrins form a rigid cage in the low-nanometer range. These individual cages are doped (coated) with a DNA-containing amorphous solution of zein. Cyclodextrin inclusion has the added benefits of being a proven and effective method of protecting active components from both oxidation and UV degradation. The cyclodextrin-casein combination is specifically chosen due to cyclodextrin's ability to inhibit casein aggregation while imparting a rigid lattice (architecture) which further aids dispersion in the presence of water; all the while, leveraging casein's adhesive affinity.

In some embodiments, cyclodextrin is added to a zein mixture at a cyclodextrin:zein ratio of about or at most 1:1, 2:1, 3:1, 4:1, 5:1, 6:1, 7:1, 8:1, 9:1, 10:1 or any intermediate ranges or values derived therefrom (e.g., the ratio is a weight ratio).

Cyclodextrin may be added after DNA taggants are added to the zein aqueous mixture. After cyclodextrin and casein are added to the zein aqueous mixture, the resulting mixture may be dried (for example, by spray drying) to form well-segregated particles by kiss-coated cyclodextrins with casein binder.

Casein

Casein, a hydrophobic globular protein, can be used in combination with cyclodextrin to significantly reduce aggregation. For example, casein can interact with both a beta-scale cyclodextrin and a surfactin lipopetide, and these components can be reacted to form a multi-lamellar nanosome structure for dispersion in aqueous systems.

Casein can be added to water in a continuous phase, which can be subsequently insinuated with a zein concentrate or mixture.

Casein may be added at 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 5%, 10% (e.g., % refers to weight percentages) or any intermediate ranges or values derived therefrom of the final aqueous composition.

Exemplary Process for Formation of Zein Solution

A non-limiting exemplary process is described below for the formation of water-dispersing, self-assembled, alcohol-free zein nanosomes.

Prior work has used alcohol/water systems upwards of 70% alcohol in order to solubilize the zein. Such systems require adding a 50% weight equivalent surfactant to the mass of zein being incorporated. This was only good as a 1% zein concentrate. The resulting "concentrate" consisted of 1% zein, 0.5% surfactant (phosphatidylcholine), and 98.5% alcohol/water (70/30). This concentrate was subsequently added to water at point-of-use in order to self-assemble zein nanosomal particles with a nominal diameter of 100 nm.

In some embodiments, the presently described composition avoids the use of alcohol. In some embodiments, the presently described composition uses [1,3]-propanediol (e.g., Zemea® [1,3]-propanediol), which is a food grade, generally regarded as safe (GRAS) corn derivative, instead of the alcohol/water system. In some further embodiments, the presently described composition uses a highly efficient surfactant, e.g., surfactin (such as that manufactured by Kaneka Corporation), instead of phosphatidylcholine, in the form of soy lecithin.

In some embodiments, a loading of zein of about or at most 1%, 2%, 3%, 4%, 5%, 6%, 7%, 8%, 9%, 10%, 11%, 12%, 13%, 14%, 15%, 16%, 17%, 18%, 19%, 20% (e.g., % refers to weight percentages) or any intermediate ranges or values derived therefrom can be used to be mixed with a non-alcohol solvent carrier such as [1,3]-propanediol to prepare a mixture. In some embodiments, a loading of [1,3]-propanediol of 20%, 25%, 29%, 30%, 39%, 40%, 49%, 50%, 59%, 60%, 69%, 70%, 79%, 80%, 89%, 90%, 99% or any intermediate ranges or values derived therefrom (e.g., % refers to weight percentages) can be used to be mixed with zein to prepare a mixture.

In one example, a 10% zein loading was used, with 1% surfactin in an 89% [1,3]-propanediol carrier such as a Zemea® carrier. When slowly added to a circulating water mass at room temperature, the concentrate disperses as a light, cloudy dispersion which increases in opacity as more concentrate is added.

Exemplary ingredients:

Zein (Flo Chemical Corp; F4401C)

Surfactant—surfactin (Kaneka)

Solvent—[1,3]-propanediol (by Zemea, or by Dupont Tate & Lyle)

Exemplary Procedure

All ingredients are weighed-out into a quartz/high silica beaker as a heating vessel. In a non-limiting exemplary embodiment, the proportions for a 10% Zein loading are: 89 grams Zemea® carrier: 10 grams zein: 1 gram surfactin (respiratory protection is used when handling surfactin due to high affinity to mucosal tissue). All measures are weight/weight and scale linearly into the final mass. The surfactin component can optionally be diluted to 0.1, 0.2, 0.3, 0.4, 0.5, 0.75, 1, 2, 3, 4, 5% or any intermediate values or ranges derived therefrom with reliable stability. Any possible combinations of Zein, [1,3]-propanediol, and optionally surfactin as described above can be used here.

The beaker is covered tightly with aluminum foil and heated on a hotplate pre-heated to an elevated temperature. For example, the elevated temperature can be at least, about or at most 90, 95, 100, 110, 115, 120, 130, 135° C. or any intermediate values or ranges derived therefrom.

The temperature of the wet solution on the hotplate is monitored with a wet probe to monitor the melt point until clarification occurs.

The batch temperature can be maintained at the elevated temperature (e.g., above 100° C.) for at least, about or at most 1, 2, 3, 4, 5, 6, 7, 8, 9, 10, 11, 12, 13, 14, 15, 16, 20, 25, 30 minutes or any intermediate values or ranges derived therefrom or until all particulates disappear. Any possible combinations of an elevated temperature as described herein and a dwell time as described herein can be used here. For example, the mixture of zein and [1,3]-propanediol, and optionally surfactin can be maintained at 115° C. for 10 minutes.

Once the solution becomes on optically clear yellow-amber, the solution is removed from heat under continued stirring. Any foaming on top is monitored, and the vortex is increased/decreased to reduce foam.

The solution is allowed to cool to room temperature as a clear amber concentrate.

The solution can then be dissolved into 45° C. water, resulting in a dispersed working dilution.

The dilution can be placed in freezing chamber with the temperature taken down to 5° C., upon which no visible agglomeration or settling occurs. When brought back to room temperature with stirring, no agglomeration or separation occurs.

Figure 1A:
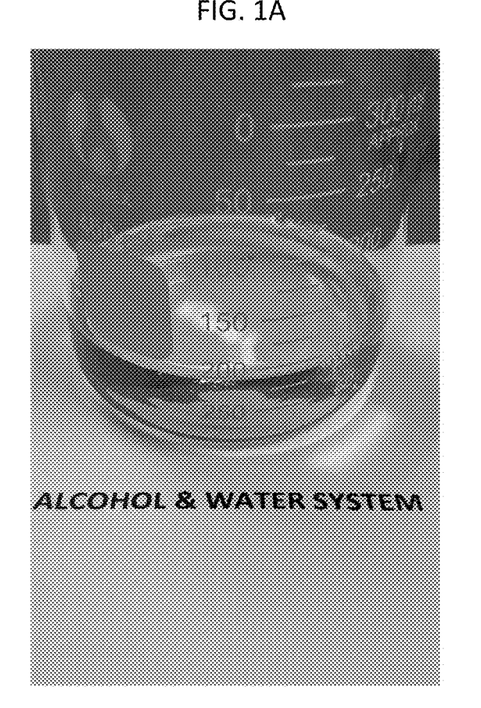
Figure 1B:
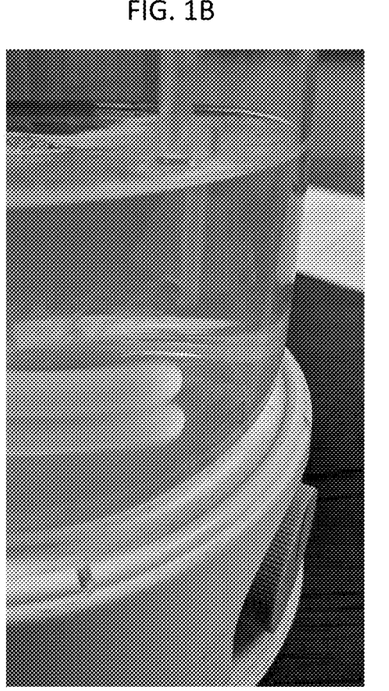
Figure 1C:
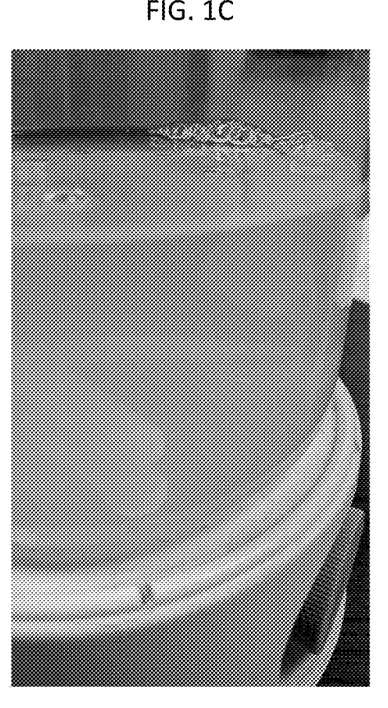

As shown in FIGS. 1A-1C, an alcohol/water concentrate including 1% zein, 60% alcohol, and 39% water was prepared. FIG. 1A shows a photograph of a mixture including zein and alcohol prior to being combined with water. This is Phase 1 of an alcohol/water process. FIG. 1B shows a photograph of the alcohol zein mixture being added into aqueous continuous phase under moderate stir, noting the dispersion plume. This shows the transition from Phase 1 (prior to adding water) going into Phase 2 (suspension in water).

FIG. 1C shows a photograph of final product from the alcohol/water dispersion process with fully self-assembled suspension in an aqueous continuous phase, i.e., Phase 2. At this step, stirring was stopped or removed. The product of the alcohol/water process is a stable, liposomal dispersion.

Figure 2A:
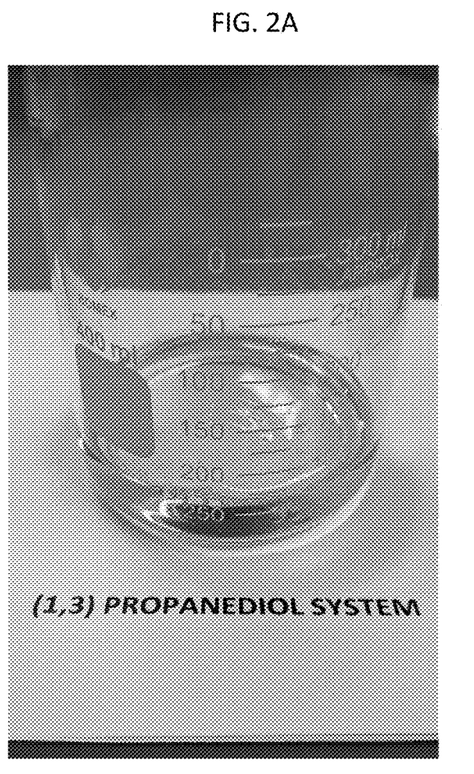
Figure 2B:
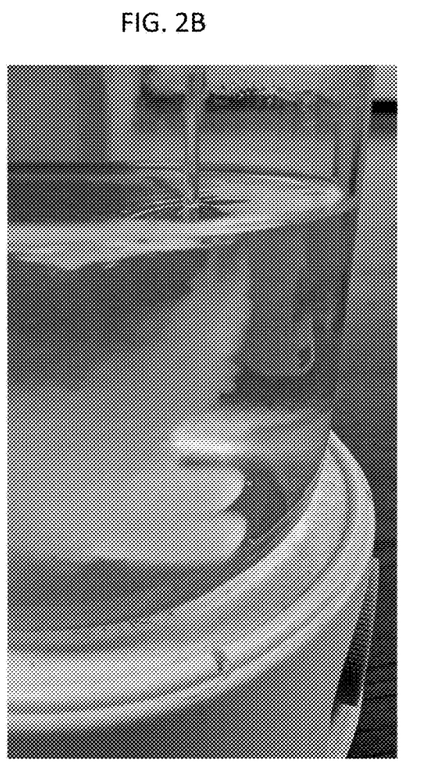
Figure 2C:
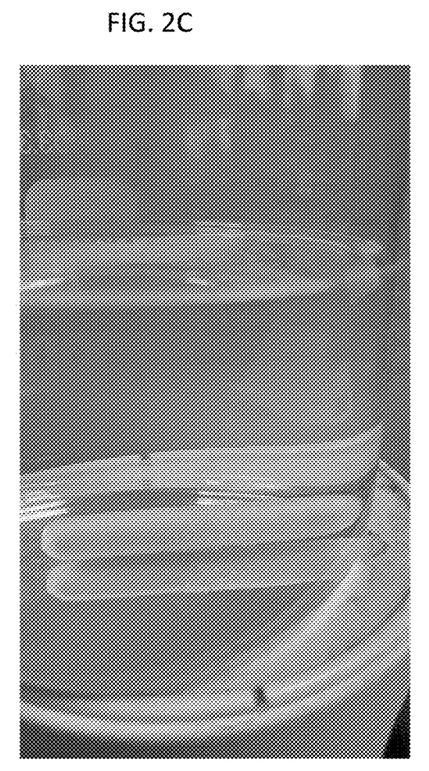

As shown in FIGS. 2A-2C, a [1,3]-propanediol/zein concentrate including 1% zein was prepared. FIG. 2A shows a photograph of a mixture including zein and [1,3]-propanediol/surfactin at an elevated temperature at Phase 1. FIG. 2B shows a photograph of the dissolution plume of Phase 1 going into Phase 2 at a temperature of 70° C. During addition of zein in [1,3]-propanediol/surfactin to water under stir, zein immediately began self-assembly with contact to water.

FIG. 2C shows a photograph of the fully self-assembled zein/propanediol/surfactin in aqueous continuous phase after a few minutes. The product of [1,3]-propanediol process is a stable, liposomal dispersion similar to the product of the alcohol/water process as shown in FIG. 1C and show even better dispersion as compared with FIG. 1C, indicating an improved solubility in water with the [1,3]-propanediol process.

Taggant Complex

This complex of DNA tags with zein, mixed with cyclodextrin, surfactin, and casein, forms a robust, stable carrier system with an affinity for hard, smooth and/or porous surfaces. This complex further allows for facile harvesting of taggant through swabbing or immersion in recovery reagent chemistries. This complex further allows for its use as a polymer component to existing food-safe applications.

Accordingly, as described herein, this technology allows for the use of zein in food products, including the recent-to-market category of generally recognized as safe (GRAS) foods, as categorized by the United States Food and Drug Administration (FDA), given the ability to solubilize the zein. Substantial work in GRAS applications is being carried out by the food and packaging industry.

Using this chemistry, compounds such as (1,3)-propanediol and the like can serve as a versatile carrier developed from corn biomass. As described herein, (1,3)-propanediol has been found to solubilize zein prolamins without depending upon the conventional and well-known method utilizing alcohol/water solvent systems.

Further, this functional coupling can act as a drop-in plasticizer to edible film-forming starches, carbohydrates, and other natural or synthetic ingredients capable of polymerizing with propanediol. This is beneficial because in many practical formulations of films and coatings, water, alcohol, and water/alcohol solutions are not suitable, as they evolve from the formulation during the heating and curing phases, leaving bubbles, air passages and weak stress areas in the product morphology.

Exemplary film and coating materials include, for example, natural polymers and synthetic polymers, such as those listed below.

Natural polymers applicable in some embodiments include, but are not limited to, the following: pullulan, starch, gelatin, pectin, sodium alginate, maltodextrin, polymerized rosin, and the like; synthetic polymers applicable in some embodiments include, but are not limited to, the following: hydroxy propyl methyl cellulose, sodium carboxy methyl cellulose, poly ethylene oxide, hydroxy propyl cellulose, poly vinyl pyrrolidone, poly vinyl alcohol, and the like.

As such, according to some embodiments, films, coatings, reinforcing polymers, etc., and the like, can be encoded as part of a comprehensive method of tracking and traceability. This can include DNA tags within and atop the product as well as the packaging materials. The set of non-coding DNA sequences used in the taggant forms a data element that can be represented by a binary word.

The existence and tracking of specific binary words can be combined with the use of public blockchains so that a relationship between a source, the binary word, the food and other relationships can be publicly posted and be unalterable. Item level traceability enables swift response to outbreaks, counterfeiting, adulteration, etc. and with this information posted to a public blockchain, it can be traced and responded to by others unrelated to the provider of the foodstuffs. This item level traceability can also be a key to fulfilling sustainability and responsible sourcing promises to consumers, as well as reducing human and economic impact of outbreaks and recalls.

Techniques described and suggested herein include methods and apparatus to apply DNA taggants to smaller batches of material from different producers before the smaller lots are aggregated into larger batches or shipments, allowing the producer of a particular unit of the material to be identified even after the smaller lots have been aggregated.

An illustrative application is in the production of palm oil, produced from the fruit of oil palms. Palm oil production raises global environmental concerns. While a purchaser of palm fruit might wish to deal with smaller vendors, perhaps even local growers, purchasers also wish to ensure that their supplier chains both produce quality fruit and are environmentally sustainable. Individual producers may produce small quantities that would be inefficient to process separately. For example, individual producers (e.g., farmers) may leave small piles of fruit to be loaded onto a truck that may pick up product from tens of producers. Without tagging, tracing a particular fruit to a particular producer is impossible, making it impossible to grade individual producers. It also allows the addition of fruit from unapproved producers, making it difficult to ensure that the only fruit used is from producers who comply with sustainable standards.

To address the above-described problems, the piles of fruit or other product may be sprayed with DNA taggants prior to collection or loading onto a truck. Each lot from each producer may receive a different DNA taggant set corresponding to a different tag string, associating individual lots with individual producers, or even identifying individual lots produced by the same producer. The taggants may be combined with a colorant to ensure uniform coverage of the product or to allow visual confirmation that the product was tagged. In some embodiments in which a product such as a fruit, pods, or leaves are attached to a branch or stem that will not be used in the primary product, the taggant may be sprayed on or otherwise applied to the stem. The smaller lots may be collected together (e.g., loaded on the same truck) and transported to a central collection and processing facility. At the processing facility, inspectors may grade or sort the fruit. For example, inspectors may place a sample, such as one fruit or a small piece of product into a bin, cup, or other receptacle, which indicates acceptable or unacceptable. If a branch or stem were tagged, the branch or stem may be placed into the bin, cup, or other receptacle. The receptacle may be sealed and transported to a processing lab for analysis of the DNA taggant set to determine a tag string that indicates the producer of the product. Producers may then be given feedback on whether their product is acceptable. In another embodiment, there may be more grades than acceptable and unacceptable (e.g., unacceptable, poor, good, excellent, or grading on a scale). Multiple grades would allow more fine-grained feedback to the producers. Producers with consistently high-quality product may be rewarded. Those with consistently low quality or unacceptable product may be asked to improve.

More generally, a DNA taggant set may be applied to a small lot of product by spraying the DNA taggant set on the product, immersing the product, or otherwise applying the DNA taggant set to the product. The DNA taggant may also be applied to a stem, branch, root, husk, or other discarded attachment of the product rather than to the processed part of the product. After the DNA taggant set is applied to the small lot of product, the small lot of product may be combined with other small lots to form a larger aggregated batch of product, large enough to be transported and processed efficiently. During processing, individual units or portions of the product may be sampled or inspected for grading. The grading may be binary (e.g., acceptable or unacceptable) or may be finer grained (e.g., unacceptable, poor, good, excellent, or grading on a scale). The grading may be done by attaching a grading label to a sample (e.g., adhesively or mechanically), by placing the sample in a labelled receptacle, or by marking the sample (e.g., with ink or paint). In an embodiment in which the taggant is applied to a stem or other attachment to the product, the attachment may be labeled, placed in the receptacle, or marked. The graded sample or attachment may be analyzed to determine the DNA taggant set, which in turn correlates to the tag string, which in turn correlates to the producer or lot, allowing the grade label from the label, receptacle, or mark to be associated with the producer or lot.

A suitable sprayer might be used, for spraying DNA taggants that are in a fluid suspension. Each grower might operate their own dispenser. That dispenser might be configured to vary the DNA taggant combination that is used over time, thus generating a unique DNA taggant combination code for each lot. In some embodiments, the grower ensures that the sprayer is thoroughly cleaned between applications to prevent cross contamination of one set of DNA taggants with another set. In another embodiment, the same DNA taggant combination may be used for a larger lot or to identify producers, and the DNA taggant combination may be changed infrequently (e.g., a few times a day). The taggant combination may be distributed from a premixed taggant combination or may be mixed in a sprayer's manifold to produce the required taggant combination.

DNA taggants correspond to encoded information that can be applied to objects, including food items, in a manner that allows for later reading of this encoded information from the objects. In a specific embodiment, the DNA taggants are unique, each taggant represents a bit position and the pattern of presence or absence of one of the DNA taggants corresponds to a bit value of 1 or 0 and the pattern of DNA taggants that are present or absent forms a binary number representing the encoded information. In another embodiment, the presence of a first DNA taggant is used to signal a value of "1" of the encoded information and the presence of a second DNA taggant is used to signal a value of "0" of the encoded information. The apparatus that adds the DNA taggants to the objects can be configured such that the encoded information can change from object to object and not cross-contaminate objects with DNA taggants that are for one object but not another.

Exemplary Implementation #1

In a specific example, there is a set of 32 DNA taggants to work with and so there are 232 possible combinations of DNA taggants that can be applied to an object, thus encoding the object with a 32-bit value corresponding to a specific "tag string" that might be represented by a sequence of 32 binary values each having a bit location in the tag string. It should be understood that other numbers are also possible and in the general case, a tag string might be represented as an indexed array of values, each having an index or position in the tag string, where the values might be binary values.

For example, it might be that 28 bits (and 28 DNA taggants) would be sufficient for a particular application. For example, if there are 128 producers of apples, each having 8 facilities, and they group their apples by lot such that they output 256 lots per year, one per day, over the course of 16 years, the manufacturer, facility, lot, and year can be encoded in a 7+3+8+4=22 bit tag string and so 22 bits and 22 DNA taggants are sufficient and that leaves room for checksum bits/taggants to be added. In this simplified example, the number of possible values for each of the variables is a power of two, but that is not required, and other values can be used. Conventional mapping of values to tag strings can be done.

As used herein, a DNA taggant is a material that includes an oligonucleotide and possibly other material. In a specific example, each DNA taggant comprises a static part and an identifier part, wherein all of the DNA taggants have the same static part and thus it can be used to differentiate between the set of DNA taggants in use and other DNA that might be present in a sample. In some embodiments, the presence of a DNA taggant can be done even when there are very low concentrations of the DNA taggant in or on the object. Thus, where there is a dispersant expected to be found in the sample, the sample and/or the dispersant thereon is sampled, detected, error-corrected as needed, etc. to determine the tag string that was applied to the object.

A tag string has an associated DNA taggant set (sometimes called a "DNA barcode"), which is a selection of particular DNA taggants used, or to be used, on an object to "label" that object with the tag string. The object might be an item being sold, bulk material, packaging, or other physical object or item where labeling according to the tag string is useful. In particular, where a printed label is not workable or viable, applying the tag string could be done instead. For illustration purposes, consider the case where the tag string comprises binary values each having a bit position in the string, such as "01101001 10101001 10100111 10010101" which has a "0" in the first bit position, "1" in the second and third bit positions, and "1" in the 32nd bit position. A specific DNA taggant is associated with each bit position of the tag string and labeling an object might comprise determining which bit positions of the tag string are "1", determining which DNA taggants go with those bit positions, and applying those DNA taggants (referred to herein as a "taggant set") to the object, and not applying the DNA taggants that go with the bit positions of the tag string that have "0" values. Alternatively, pairs of DNA taggants might be used, wherein the presence of one taggant indicates a "1" in a position and the presence of the other indicates a "0" in that position. Though this approach uses twice as many taggants for the same number of bits of information, it provides error checking. Other approaches used error checking codes are possible.

The tag string could represent different information. For example, in a particular industry or application, some of the bit positions might correspond to the company name, others to a serial number, others to a production date or location, etc. By later sampling the object on which the taggant set was applied, a tag detecting system can decode the taggant set and from there determine the tag string that was applied to the object.

In some embodiments, all or part of the tag string is an index value that points to a record in an external database that provides data about that particular record. In those embodiments, the tag string assigned to an object might be entirely arbitrary and an external database of object information would be used to get data about the object rather than decoding any data about the object from the bit pattern itself.

In an example distribution system, there are lots and each lot has applied to it a specific tag string and a first lot receives a first taggant set corresponding to a first tag string and then a second lot receives a second taggant set corresponding to a second tag string different than the first lot. The first lot might be multiple items, such as a plurality of melons, or the first lot might be a single item, such as a bag of coffee beans. In the case of a bag, the distribution system might be integrated in with an automated bag filling line. In such a line, a new bag is positioned in the system and is clamped to the filling line chute to receive product. Perhaps before the first bag is in place, the distribution system initially dispenses plain carrier (no taggants) in the "dead volume" (the volume of the piping beyond actuating valves). Then when the empty bag is in place, or after the bag is filled, but before it is declamped and stitched closed, the distribution system actuates certain valves of the distribution system to push out the plain carrier and then push out specific taggants based on that bag's designated tag string. It may be that delivery is timed so that the plain carrier residing in the dead volume is delivered during clamping to the bottom of the empty bag and the taggants are delivered as the product is filling the bag. The taggant valves may be de-energized before the bag is full while the plain carrier valve remains energized, so that at the completion of the bag filing cycle, the dead volume has been filled by plain carrier, at which point the plain carrier valve is de-energized. The cycle repeats with a new taggant combination for the second bag and so on with the plain carrier effectively flushing the lines so that only the desired taggants appear for a given lot.

Instead of a spray, the carrier/taggants might be applied by immersion.

The DNA tags can be applied in a complex with zein, cyclodextrin, casein, and surfactin which can be coated to a product directly or mixed with another coating material (e.g., carnauba wax ethanol, water, etc., and the like). Studies have shown DNA stability is greater when included in some persistent matrix, as in the presently described complex with zein, cyclodextrin, casein, and surfactin.

As described herein, the final taggant is non-thermally reversible and maintains a homogenous dispersion for a period of time adequate for industrial application of DNA tags. Further, it no longer exhibits the self-binding and agglomeration problems inherent with zein-in-water systems Zein has been actively researched and validated as a preferred carrier of DNA. See, for example, Taylor et al., *J. Nanobiotechnology,* 2012, 10, "Fabrication and Characterization of DNA-Loaded Zein Nanospheres".

Encapsulation of the taggant in a solid carrier (such as cyclodextrin) can provide superior stability that is usually in excess of one or two years. The solid form is a convenient form for application of taggants to dry and granular products such as flour, sugar, etc. Taggants encapsulated in solid matrixes (such as cyclodextrin) can also be used in processed foods and liquids (e.g., juices, oils, etc.) encapsulated in a solid matrix that does not dissolve in the product, as that would release the DNA of the taggant and may limit its stability.

For commodities such as fertilizers, beans, grains, etc., application of taggants in solid form (encapsulated, e.g., in a matrix such as cyclodextrin) might be used due to stability considerations. However, for high speed processes, as when, for example, a taggant must be uniformly applied to product during the bag filling process (which might be a two to four second cycle), liquid carriers might be used instead of powder but liquid carriers can be very difficult to manage at those high speeds and prone to cross contamination. A cost-effective method to apply a taggant in solid form is as very fine powder, which increases the number of taggant particles per volume of product. This increases the probability that the taggant will be recovered from a small sample of product when the product is tested for the presence of the taggants. However, when fine particles are used, they may remain airborne for minutes or even hours, possibly migrating to lots where they were not intended to be applied, which would cause identification errors when taggant reading is done on a sample of the product. Loose particles also might cause cross-lot contamination at the point of testing as the product is taken out of a bag. In these situations, application of the taggants in a liquid form would simplify the application process but might result in diminished stability.

In an improved application process, a hybrid method is used that combines the ease of the liquid application with the stability of the solid carriers. In this approach, the taggant is encapsulated in powder granules, such as any composition described herein, for example, a composition comprising prolamin in a complex with encapsulating carriers such as cyclodextrin, that are suspended in a liquid in which the granules do not dissolve. Non-limiting additional and alternative examples of encapsulating carriers include gelatins, agarose gel, carrageenan powder, etc. and the liquid carrier might be ethanol. Another example is ethyl cellulose powder as the encapsulating carrier and water as the liquid carrier.

The distribution system can then spray a product or immerse the product, thus improving uniform application and reducing the potential for loose powder and resulting cross contamination. The amount of liquid carrier required is usually very small (in one example, less than 50 mL per 50 kg bag). The liquid carrier either evaporates or is absorbed by the product leaving the taggant as an encapsulated powder in the sealed bag.

In addition, use of gels promotes adhesion of the powders to the product, reducing the risk of contamination due to loose powder when the bag is opened. Other adhesives may be added to the liquid to promote adhesion. For example, applying ethyl cellulose powder suspended in a 0.5% agar-agar solution will create a film containing ethyl cellulose DNA tagged powder on the surface of the product.

A dispensing system might include tanks or vessels that contain one of the DNA taggants (or taggants in encapsulating carriers) in suspension, powder, or other forms such as emulsions, liposomes in liquid, or coacervations (a type of electrostatically-driven liquid-liquid phase separation, such as spherical aggregates of colloidal droplets held together by hydrophobic force measuring from 1 to 100 micrometers across or some other diameter, while their soluble precursors are typically on the order of less than 200 nm or some other distance). A computer control system might control the dispensing of specific patterns of the DNA taggants. The taggant vessels have a finite volume and so DNA taggant gets consumed. By careful selection of which patterns are used, the consumption can be controlled so that the taggant vessels do not need to be filled at inconvenient times.

The dispensing system might be required to deliver distinct taggant sets (thus marking distinct objects or lots with different tag strings) at very high speed, as many as 20-25 per minute or more. In an implementation, a computer processor determines what tag string is to be applied and then sends electrical signals and commands to various modules, ultimately resulting in the desired taggant set being added or applied to the object being marked. It may be that each object marked gets a different taggant set, so the dispensing system would carefully control the distribution of taggants so that the taggants of the taggant set applied to a current object do not get used during application of a next object (unless those are taggants that are part of the taggant set for both the current object and the next object).

Exemplary Implementation #2

In an example implementation, a taggant corresponds to a 28-bit binary word, but in some embodiments, it could be a 16-bit binary word, a 40-bit binary word, or some other length. Each bit position in the word corresponds to a particular non-coding DNA sequence, such that the presence in the taggant of that particular non-coding DNA sequence is interpreted as the label for that tagged item having a "1" in the bit position of the word that, by perhaps predetermined designation, is assigned to be associated with that particular non-coding DNA sequence.

A non-coding DNA sequence might comprise around 50 to 200 base pairs in a sequence, or may comprise 5, 10, 20, 30, 40, 50, 60, 70, 80, 90, 100, 200, 500, 1000, 2000 base pairs or any intermediate ranges or values in a sequence. The taggant might comprise a plurality of the non-coding DNA sequences, in a very low concentration, in a complex with zein, cyclodextrin, casein, and surfactin, which can be coated to a product directly or mixed with another coating material (e.g., carnauba wax ethanol, water, etc., and the like). The particular non-coding sequences ("tags") might be unique to the environment, such as drawn from seaweed when used for tagging foods other than seaweed. The tag sequences might be non-coding, non-viable, non-toxic, generally regarded as safe oligonucleotide. The tag sequences might be microencapsulated in edible particles and/or mixed with carrier liquids. In effect, the collections of tags form "barcodes" by combining multiple DNA tag sequences in unique combinations.

Figure 3:
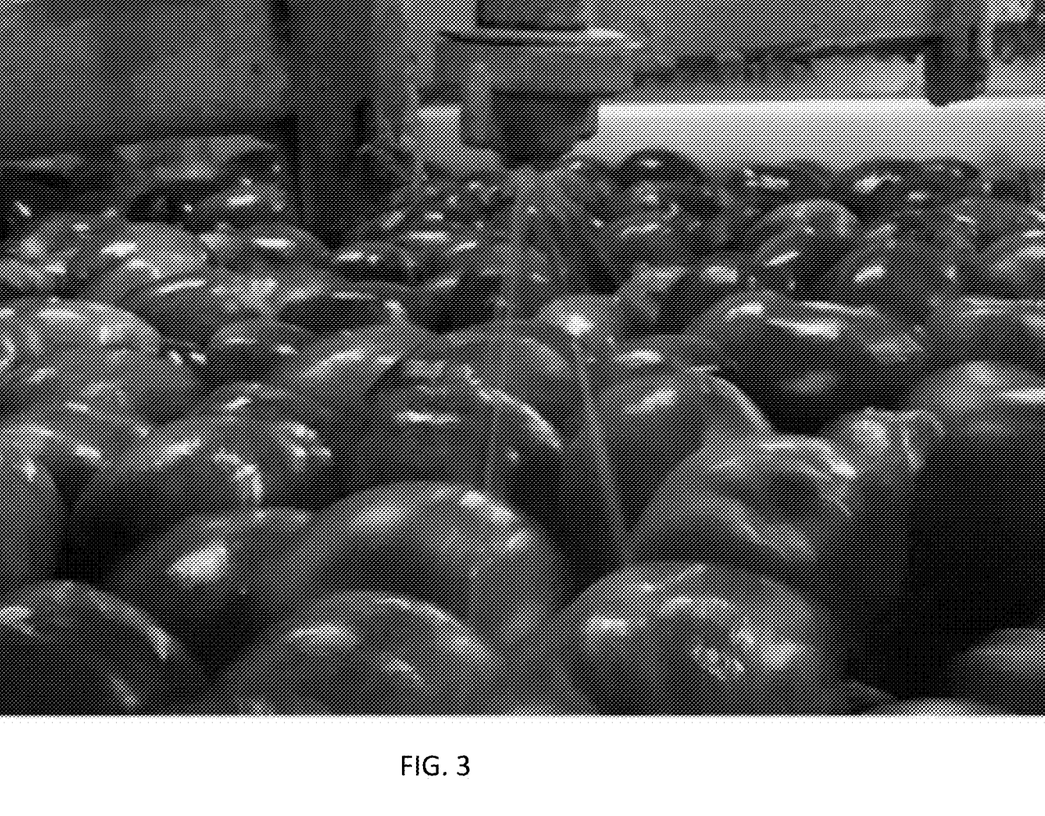
FIG. 3 illustrates how a taggant might be applied during existing production processes in accordance with some embodiments.

FIG. 3 illustrates how a taggant might be applied during existing production processes. The taggant might comprise the tag sequences in any composition described herein, which can be coated to a product directly or mixed with another coating material (e.g., carnauba wax ethanol, water, etc., and the like). For example, the taggant might comprise the tag sequences in a complex with zein, cyclodextrin, casein, and surfactin, which can be coated to a product directly or mixed with another coating material (e.g., carnauba wax ethanol, water, etc., and the like). In tests, the label (i.e., the binary word encoded by the presence or absence of particular DNA tag sequences in the taggant applied) was readable without error even after 6 months of refrigeration. Where differently labeled apples are commingled, correct identification with high reliability is still possible. Stability over time might be as much as several years.

Figure 4:
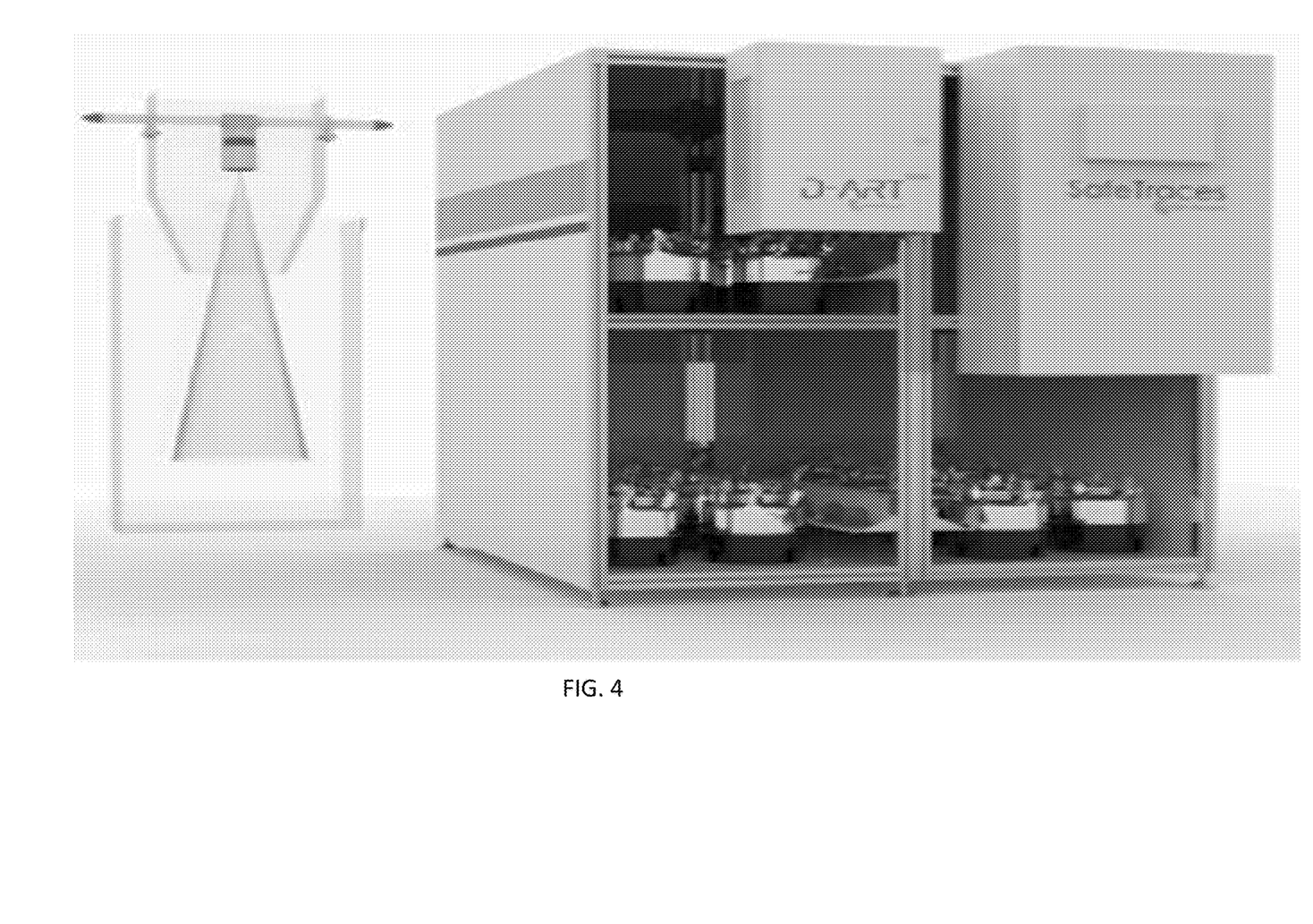
FIG. 4 illustrates a non-limiting example of a computer-controlled tank system, in accordance with some embodiments, that might be provided with a designated label and then control which tanks containing tag sequences are opened and tag sequences mixed to form the taggant that is to be applied.

FIG. 4 illustrates an example of a computer-controlled tank system that might be provided with a designated label and then control which tanks containing tag sequences are opened and tag sequences mixed to form the taggant that is to be applied.

Such a dispensing system might be able to apply a unique label (e.g., a unique DNA barcode) every three seconds, i.e., be able to switch between unique labels in a production process as fast as every three seconds while ensuring that one batch that is supposed to get one label and the next batch that is supposed to get a different label do not get labels "bleeding" over from batch to batch. Where the labels correspond to 28-bit binary words, there are over 250,000,000 possible unique labels. With error correction included, the binary words could be longer or the codeword space could be less than $2^{28}$ codewords.

The dispensing system might be used on fruits, nuts, grains, other agricultural products, or other produced materials. With the nature of the taggant, the materials could be bulk granular material, liquids, etc. For example, taggant might be used to label ammonium nitrate fertilizer at the point of production to help track cases of production of improvised ammonium nitrate explosives to determine their source of ammonium nitrate. As the taggant applied is so low volume, it would not be expected to affect the uses of the materials.

The taggant might be applied to equipment and surfaces in food safe particles that mimic pathogen behavior, such as bacteria behavior. Such particles might attach, detach, transfer and degrade in the presence of sanitizers in the same manner as the target bacteria and the survival of the taggant-laden particles can be tested for at various times. This can easily integrate at scale into existing sanitation and produce wash processes and enable on-site validation, rapid verification, and monitoring of sanitation processes.

Figure 5:
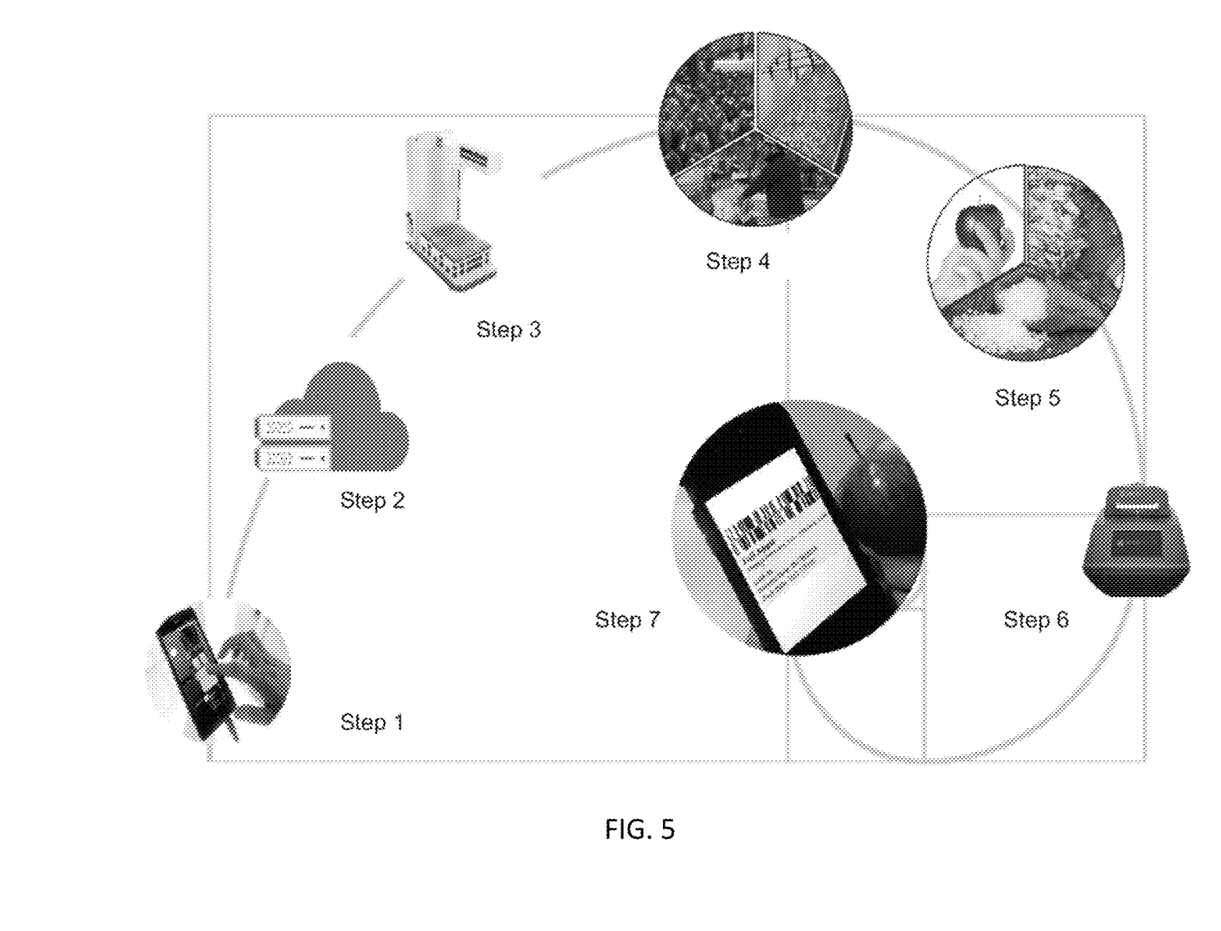
FIG. 5 illustrates a non-limiting exemplary process flow in which the non-coding DNA sequences and taggants might be used in accordance with some embodiments.

FIG. 5 illustrates a process flow in which the non-coding DNA sequences and taggants might be used. At step 1, data is entered such as lot information and other details pertinent to a batch of material to be labeled with taggant. This might be done via a cloud-connected interface such as a tablet usable on a production floor. At step 2, this information is conveyed to a server that can record the details (for later use in interpreting read labels, for example), authenticate a request and generate an instruction set to be sent to a taggant dispenser that is network-connected. Information might also be recorded in a transaction on a public blockchain so that the instruction set cannot be later altered without detection.

At step 3, the taggant is created from the combination of tag sequences that is consistent with the provided instruction set. At step 4, the taggant is dispensed onto the food products or items to be tagged. At step 5, a sample is collected for testing. At step 6, samples can be analyzed using PCR or other techniques. Then, at step 7, the results of the analysis can be provided.

The results of the analysis might be done by, in step 6, first determining which tags were present or absent. Then, as part of step 7, the presence or absence of tags is represented by a binary word and that binary word is used as a lookup (or the information is encoded directly in the binary word) perhaps by reference to the server mentioned in step 2 or by reference to a public blockchain. In that manner, the labeling of a product can be done from source to consumer, regardless of the changes or absence of packaging or conventional labels.

The tags-identity associations can be placed on a public blockchain, thus allowing unrelated parties to check a product in a supply chain, independent of the labels applied by intermediaries and the labeling of food products are not limited to labels on the pallet, box, or bag. This would allow third parties to make informed decisions in the event of a recall regarding affected lots, and provides for improved facility and product sanitation based on impact on product quality, shelf life, and safety.

For example, a grain producer might be running an app on a smartphone or tablet and input into the app details of a batch of grain (e.g., time of production, name of company, production details, type of grain, supervisor name, serial number and network address of their taggant dispenser, etc.). The app might then send those details in a data record to a server that records the details, assigns a unique label (in the form of a binary word, for example, to be used as a DNA "barcode"). The server might also maintain a database of the particular sequences of nucleotides that are in each of the tags that are in the tanks of the taggant dispenser that that grain producer is operating. The server might then send, as a network message, the identified dispenser a listing of the unique label to be used for that batch. Of course, this process might be done for multiple batches at a time, where the grain producer operator inputs data for several batches and their dispenser receives several unique labels. Since the dispenser is programmed to understand how to mix tags in taggant according to the bits of the unique label, the dispenser can provide taggant that in effect labels the grain with the unique label.

The time of production, name of company, production details, type of grain, supervisor name, batch size, expected customer (if available), serial number of taggant dispenser, the unique label assigned, the code alphabet (which indicates which binary words are valid binary sequences), the error correction used (if any), the taggant suspension and type used (e.g., zein, cyclodextrin, casein, and surfactin; additional components can include water, powder, microcapsules, wax, alcohol, etc.) and the sequences of DNA nucleotides used for all of the DNA tags that might have been used in codewords, as well as other details as needed, might all be recorded in one data record that is then inserted into a blockchain transaction and signed by the provider of the taggant dispensers. Once this blockchain transaction is posted to a public blockchain ledger, it cannot be easily altered without others noticing. In this manner, the pertinent details about the labeling using the non-coding DNA sequences are made a public record that any third party could use. For example, suppose a regulator or food safety official traces an illness outbreak to a particular food item and there are samples of the food item available for testing. The regulator could collect the sample and test it to determine if it was labeled, perhaps by detecting a static portion of non-coding DNA sequences known to be in use. If it was labeled, they could look to the public ledger for a transaction containing the details of the production and without having to resort to research and identifying and getting the cooperation of many different parties in a supply chain can simply look to the blockchain ledger to identify the batch number and producer of the food in question.

In the manner described above, production processes and tracking processes are improved. Examples described herein provide for a method and apparatus for tagging items comprising applying a plurality of non-coding DNA tags, wherein the selection of the particular tags corresponds with a binary or nonbinary code sequence containing information about the tagged items and wherein a non-coding DNA tag comprises a DNA sequence that would not otherwise be present in the tagged item. The items tagged can be food items and the information can include information as to a source of the food items. The items tagged might be surfaces requiring sanitary handling, where the information includes information as to whether the surfaces were sanitized sufficiently. DNA tags might be selected from among a set of DNA tags with the selection representing and/or corresponding to a label that is a binary word with bits in bit positions corresponding to whether a particular DNA tag was selected. The selection of DNA tags might be combined with a carrier to form a taggant that is applied to surfaces requiring sanitary handling or items to be tagged. The carrier of the taggant can include zein, cyclodextrin, casein, and surfactin and can further include air, water, alcohol or other volatile substance, a wax, a powdering agent, and/or microbeads.

A method might provide for tagging items comprising applying a plurality of non-coding DNA tags, wherein the selection of the particular tags corresponds with a binary or nonbinary code sequence containing information about the tagged items, substantially as shown herein. An apparatus for tagging items might comprise apparatus for applying a plurality of non-coding DNA tags, wherein the selection of the particular tags corresponds with a binary or nonbinary code sequence containing information about the tagged items, substantially as shown herein. An apparatus might be provided for reading tags from tagged items tagged with a plurality of non-coding DNA tags, wherein the selection of the particular tags corresponds with a binary or nonbinary code sequence containing information about the tagged items, substantially as shown herein. Details of the tags might be recorded in a public blockchain transaction.

Exemplary Implementation #3—Sanitation and Tracing Combined

In an example embodiment, these techniques could be used for tracing a product to its origins or other point in a supply chain it passes through, testing for efficacy of a sanitation process, or both, with information provided in a public manner to allow for independent testing and assessment.

As explained herein and here, a process might start with the selection of a tag to be applied. This tag might be for applying to a product or a surface for later detection without requiring packaging or visible labeling or alteration. The tag might be represented by, and correspond to, a unique sequence of characters. In some embodiments, each character is selected from a binary alphabet, so that the sequence of characters is a bit sequence. In other embodiments, the alphabet has more than two possible characters. An example of such a tag might be a 28-bit, 32-bit, or 60-bit value. In the sequence of characters, each character has a value and a sequence position (e.g., there might be a "1" in the 45th position in the character sequence and a "0" in the seventh position in the character sequence).

Then, there might be a set of noncoding DNA snippets, wherein one of the DNA snippets is associated with one of the character values at one of the character positions. For example, there might be 120 DNA snippets to select from, where 60 DNA snippets are DNA tags for the 60 possible character positions that could have a character value of "1" and 60 other DNA snippets are DNA tags for the 60 possible character positions that could have a character value of "0". In some variations, some of the character values could be represented by the absence of any of the set of DNA snippets. For example, it could be that there are 28 bit positions in the tag and the set of DNA snippets that make up the DNA tag are 28 DNA snippets and where a character position has a character value of "1", the corresponding DNA snippet of the 28 DNA snippets is present and when that character position has a character value of "0", none of the 28 DNA snippets are present. In the general case, where there are M possible characters per character position, and there are N positions, there are M^N possible distinct tags.

A material can be formulated that contains a carrier including zein, cyclodextrin, casein, and surfactin, as well as the DNA snippets that correspond to the tag. This material can be applied to a product to be able to trace the product, to a surface to be able to later test for sanitation efficacy, or to a product that is later washed and shipped, to be able to determine both how well it was washed and where it originated.

The tag and additional information about the product or surface can be posted to an unalterable blockchain ledger and at a later time, a sample can be taken from the product or surface, and tested to identify which of the noncoding DNA snippets are present and then the blockchain ledger read to find the blockchain transaction that has the additional information about the product or surface that corresponds to the unique sequence of characters represented by the DNA snippets found in the sample.

Additional Exemplary Implementations

The zein complexes described herein or any composition described herein can be used in a range of additional areas, unrelated to tracking. These include, but are not limited to, the following areas:

Packaging materials of woven and non-woven cellulosic and other fiber materials. Relevant products include, for example, loose-laid and molded formats, i.e., clamshell, food liners, etc., and the like.

Waterborne discrete zein particles, either liposomal or nanosomal, can be readily absorbed into fiber and cellulosic architecture matrices. Upon drying, the polymer coating lends hydrophobicity to the materials. The concentration of this formula can be adjusted in the self-assembly phase to allow for a variety of surface densities, thus enabling apertures in the coating to provide for enhanced moisture-vapor transfer rates (MVTR). This can be important in applications where packaging or protective materials are designed to breathe.

Sheet paper goods. Such products include products of spinneret, electrospinning, blow-spinning, and extrusion production, as well as foams, castings, and molded products.

The presently described zein complexes can be used to produce cast and calendar-finished sheet goods, with varying degrees of resistance to inks and moisture. Such polymers can be adhered onto monofilament processes prior to spinning into yarns, for example.

Additionally, extrusions can be made wherein the elevated flux values allow for efficient flashing-off of the aqueous carrier, leaving a well dispersed zein. Foams, such as water-based two-part urethanes, castings, such as polyvinyl alcohols, and molded structures, such as those comprising styrene maleic anhydride all utilize "cleaner" processes as aqueous solutions. The presently described water-based zein complex can be utilized with greater simplicity and worker safety.

Personal care, dermal, medical, and cosmetic products. Due to zein's film-forming affinities, water-soluble systems can be incorporated in a range of personal care products, including moisturizing products (as an anchoring humectant), hair care products (providing cuticle binding and smoothing properties), wound care (allowing for site protection and drug elution), and many others.

Heretofore, personal care, dermal and cosmetic formulations have been reliant on synthetic solubilizers, such as surfactants and hydrocarbon-based solvents, for imparting efficient dispersion, phase stability, and organoleptic/sensory qualities. By incorporating actives into the zein architecture, industry formulators can provide their products with new properties such as dermal compatibility, in unique formulations.

Improvements in humectancy can be achieved by imparting skin surface hydrophobicity, thus controlling MVTR across the dermis, for example.

Hair products can be formulated without relying upon problematic alcohol-based solutions, which tend to degrade color treatments while simultaneously drying keratin tissue. Nanosomal zein can be applied within the hair cuticle simply by promoting absorption into the cuticle surface plates, thus imparting strength, body, and control during the sculpting process.

Clinical applications in wound care can be exploited by utilizing a zein-treated platform with sufficient MVTR to enhance drug delivery via controlled-release elution, while promoting the required aerial conditions for tissue granulation. This can be in the form of zein-treated fibers and foams as well as therapeutic formulations in the form of controlled rheologies ranging from water-thin to serums, poultices, and pastes, and the like.

Further advantages can be derived by utilizing this zein technology in controlled dissolution films from cellulosic polysaccharides, such as nanocellulose as well as maltotriose film formers, such as pullulan, and the like, for example.

Metal protective coatings. Water-dispersion properties can be useful after the product has dried upon hard surfaces, thus creating novel and worker-safe metal protective coatings for both home and industry.

Upon curing, zein films can withstand moderate aqueous wash in order to provide protection from oxidation. This is especially true in the industrial setting where routine humidity levels from dew-point transitions can degrade valuable raw materials.

Food applications. The presently described zein complexes can be used in food applications for both human consumption and animal feeds due to zein's coating efficiencies. Even small granule dimensions can be coated utilizing Wurster, pan, fluidized bed, etc., coating technologies. Once treated, granules, prills, pellets, powders, and the like, can benefit from enhanced flow and non-binding improvements.

Bulk food preparations can benefit from protective coating in the form of zein which has been incorporated prior to packaging. This can greatly delay degradation due to oxidation, elevated moisture, and even biological activity.

Coatings. Prolamin compositions described herein, such as water-soluble zein, in varying concentrations can be applied as a coating to further provide surface protection as a graffiti protectant, in sandblasting and etching operations, in ablative masking, etc.

Semi-permanent coatings can be applied using prolamin compositions described herein, such as water based zein, in areas where the surface must be routinely scoured and renewed as well as surfaces which must be masked prior to applying more durable finishes or passivation coatings.

Hardware Implementations

According to one embodiment, the techniques described herein are implemented by one or more generalized computing systems programmed to perform the techniques pursuant to program instructions in firmware, memory, other storage, or a combination. Special-purpose computing devices may be used, such as desktop computer systems, portable computer systems, handheld devices, networking devices or any other device that incorporates hard-wired and/or program logic to implement the techniques.

The use of any and all examples, or exemplary language (e.g., "such as") provided herein, is intended merely to better illuminate various embodiments and does not pose a limitation on the scope of various embodiments unless otherwise claimed. No language in the specification should be construed as indicating any non-claimed element as essential to the practice of various embodiments.

In the foregoing specification, various embodiments have been described with reference to numerous specific details that may vary from implementation to implementation. The specification and drawings are, accordingly, to be regarded in an illustrative rather than a restrictive sense. The sole and exclusive indicator of the scope of various embodiments, and what is intended by the applicants to be the scope of various embodiments, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed embodiments can be advantageously made. The example arrangements of components are shown for purposes of illustration and it should be understood that combinations, additions, re-arrangements, and the like are contemplated in alternative embodiments. Thus, while the disclosure has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the various embodiments as set forth in the claims and that the disclosure is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. A composition comprising prolamin and [1,3]-propanediol.

2. The composition of claim 1, wherein the prolamin comprises zein.

3. The composition of claim 2, wherein the zein comprises zein nanoparticles.

4. The composition of claim 1, wherein the composition is essentially free of ethanol.

5. The composition of claim 1, wherein the composition further comprises a surfactant.

6. The composition of claim 5, wherein the surfactant comprises surfactin.

7. The composition of claim 1, wherein the composition is in an aqueous solution.

8. The composition of claim 1, wherein the composition further comprises cyclodextrin.

9. The composition of claim 1, wherein the composition further comprises casein.

10. The composition of claim 1, wherein the composition further comprises one or more stabilizers.

11. The composition of claim 1, wherein the composition is a powder.

12. The composition of claim 1, wherein the composition further comprises a DNA taggant set and the DNA taggant set comprises a unique combination of a plurality of DNA sequences.

13. A method of preparing a composition, the method comprising:
  a) obtaining a first solution comprising prolamin and [1,3]-propanediol;
  b) obtaining a second solution comprising water; and
  c) mixing the first solution with the second solution to prepare the composition.

14. The method of claim 13, further comprising mixing the prolamin and the [1,3]-propanediol at a first elevated temperature to form the first solution.

15. The method of claim 13, wherein the prolamin of the first solution comprises zein, and the second solution further comprises cyclodextrin, surfactant, and casein, in an aqueous carrier solution.

16. The method of claim 13, further comprising mixing the prolamin with a surfactant in the [1,3]-propanediol at a first elevated temperature to form the first solution.

17. The method of claim 16, wherein the first elevated temperature is a temperature between 90 and 115° C.

18. The method of claim 13, further comprising adding a surfactant to zein and [1,3]-propanediol to obtain the first solution.

19. The method of claim 13, further comprising adding DNA to the first solution before adding the first solution to the second solution.

20. The method of claim 19, wherein the DNA comprises a unique combination of a plurality of DNA sequences.

* * * * *